United States Patent
Kaneria

(10) Patent No.: US 12,347,551 B1
(45) Date of Patent: Jul. 1, 2025

(54) SYSTEMS AND METHODS FOR PREDICTIVE ANOMALY DETECTION IN PHARMACEUTICAL PROCESSING DATA

(71) Applicant: Express Scripts Strategic Development, Inc., St. Louis, MO (US)

(72) Inventor: Ankur Kaneria, Cedar Park, TX (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 1214 days.

(21) Appl. No.: 17/118,872

(22) Filed: Dec. 11, 2020

(51) Int. Cl.
| | |
|---|---|
| G16H 40/20 | (2018.01) |
| G06N 20/00 | (2019.01) |
| G08B 21/18 | (2006.01) |
| G16H 10/60 | (2018.01) |
| G16H 20/10 | (2018.01) |
| G16H 50/70 | (2018.01) |
| H04L 9/40 | (2022.01) |
| G06K 7/10 | (2006.01) |
| G06K 7/14 | (2006.01) |
| G06Q 10/08 | (2024.01) |
| G06Q 10/10 | (2023.01) |
| G06Q 30/0601 | (2023.01) |
| G06Q 40/08 | (2012.01) |
| G06Q 40/12 | (2023.01) |
| G16H 70/40 | (2018.01) |

(52) U.S. Cl.
CPC ............ *G16H 40/20* (2018.01); *G06N 20/00* (2019.01); *G08B 21/18* (2013.01); *G16H 10/60* (2018.01); *G16H 20/10* (2018.01); *G16H 50/70* (2018.01); *H04L 63/1416* (2013.01); *G06K 2007/10504* (2013.01); *G06K 7/1413* (2013.01); *G06Q 10/08* (2013.01); *G06Q 10/10* (2013.01); *G06Q 30/0633* (2013.01); *G06Q 40/08* (2013.01); *G06Q 40/12* (2013.12); *G16H 70/40* (2018.01)

(58) Field of Classification Search
None
See application file for complete search history.

(56) References Cited

U.S. PATENT DOCUMENTS

| | | | |
|---|---|---|---|
| 8,161,554 | B2 | 4/2012 | Sadhasivam |
| 9,936,916 | B2 | 4/2018 | Sahin |
| 10,210,470 | B2 | 2/2019 | Datta Ray |
| 10,348,997 | B2 | 7/2019 | Trepanier |

(Continued)

*Primary Examiner* — Devin C Hein
(74) *Attorney, Agent, or Firm* — Jordan IP Law PC

(57) ABSTRACT

A monitoring server is provided for learning event patterns in pharmaceutical order processing and identifying anomalous events based on learned event patterns. The monitoring server is configured to define a plurality of feeds of monitoring data from the monitored nodes using a monitoring link. The feeds of monitoring data are defined at least partially based on the monitoring vector definition. Each feed of monitoring data is associated with pharmaceutical order processing. The processor is additionally configured to determine a set of monitoring vector data for each of the plurality of feeds of monitoring data. The processor is also configured to identify a monitoring vector signature for each of the plurality of feeds. The processor is also configured to identify an anomalous data pattern. The processor is also configured to transmit an alert indicating that pharmaceutical order processing for the associated feed of monitoring data is anomalous.

20 Claims, 7 Drawing Sheets

(56) References Cited

U.S. PATENT DOCUMENTS

| | | |
|---|---|---|
| 10,757,124 B2 | 8/2020 | Saraf |
| 10,776,890 B1* | 9/2020 | Samarin ................. G06Q 50/22 |
| 10,931,635 B2 | 2/2021 | Rhee |
| 12,046,343 B1* | 7/2024 | Zagami .................. G16H 10/60 |
| 2015/0081324 A1* | 3/2015 | Adjaoute ............... G06Q 40/08 |
| | | 705/2 |
| 2017/0308917 A1 | 10/2017 | Winters |
| 2017/0339178 A1* | 11/2017 | Mahaffey ............ G06F 11/3006 |
| 2019/0028509 A1 | 1/2019 | Cidon |
| 2019/0319971 A1* | 10/2019 | Levy ................... H04L 63/0807 |
| 2020/0322367 A1 | 10/2020 | Salvat Lozano |
| 2020/0358804 A1 | 11/2020 | Crabtree |
| 2021/0224918 A1* | 7/2021 | Heyrani-Nobari .......................... |
| | | G06F 18/2433 |

\* cited by examiner

SYSTEMS AND METHODS FOR PREDICTIVE ANOMALY DETECTION IN PHARMACEUTICAL PROCESSING DATA

FIELD OF INVENTION

The field relates to predicting anomalies in complex computing systems and, more specifically, to systems and methods for identifying complex patterns in node vectors and dynamically identifying anomalous or abnormal events that may cause process failure.

BACKGROUND OF THE DISCLOSURE

In modern computing systems, many computing devices and virtual devices often work together to process information. In many examples, such systems are dynamic and involve additions of or interaction with new devices on a regular basis. Such dynamic changes may often change the normal course of data processing and the expectations for how information can be processed.

In the specific context of pharmaceutical prescription processing, dynamic changes pose challenges to efficient information processing, communication, and logistics. Because of the complexity of requirements for data processing in pharmaceutical prescription processing, there are complex rule sets that are applied to successfully cause the fulfillment and payment processing of prescription drugs. However, the addition of new computing devices for particular pharmacies, insurers, manufacturers, or other parties may change the normal processing of information. As such, adding new clients, pharmacies, drugs, providers, and members may cause significant change. In some cases, such additions may create elevated risks of failed, abnormal, or anomalous processing. A related and underlying problem is an inability to identify what constitutes "normal" behavior for particular types of data and to understand whether new systems or programs use models that conform to preexisting norms.

Existing methods of addressing such problems in information processing are deficient because they rely upon diagnostics after failures have occurred. However, waiting until data processing fails has significant consequences for the efficiency of the system and the participants involved. Further, the ability to identify anomalous patterns before they create significant failures may increase system efficiencies.

Accordingly, a solution to these technical problems is desired that can provide methods for identifying complex patterns in node vectors and dynamically identifying anomalous or abnormal events that may cause process failure.

BRIEF SUMMARY OF THE INVENTION

In one aspect, a monitoring system is provided for learning event patterns in pharmaceutical order processing and identifying anomalous events based on learned event patterns. The monitoring system includes client computing devices and a monitoring server. Each client computing device includes a client processor and a client memory. The monitoring server is in communication with the client computing devices. The monitoring server includes a processor and a memory. The processor is configured to establish a monitoring link to the monitored nodes. The monitoring server is configured to define a plurality of feeds of monitoring data from the monitored nodes using the monitoring link. The feeds of monitoring data are defined at least partially based on the monitoring vector definition. Each feed of monitoring data is associated with pharmaceutical order processing. The processor is also configured to receive the plurality of feeds of monitoring data using the monitoring link. The processor is additionally configured to determine a set of monitoring vector data for each of the plurality of feeds of monitoring data. The processor is also configured to identify a monitoring vector signature for each of the plurality of feeds of monitoring data. Each monitoring vector signature defines a range of monitoring vector data is created by a trained predictor. The processor is also configured to identify an anomalous data pattern upon determining that at least one of the set of monitoring vector data is outside the range of the monitoring vector signature for the associated feed of monitoring data. The processor is also configured to transmit an alert indicating that pharmaceutical order processing for the associated feed of monitoring data is anomalous.

In another aspect, a monitoring server is provided for learning event patterns in pharmaceutical order processing and identifying anomalous events based on learned event patterns. The monitoring server is in communication with client computing devices. The monitoring server includes a processor and a memory. The processor is configured to establish a monitoring link to the monitored nodes. The monitoring server is configured to define a plurality of feeds of monitoring data from the monitored nodes using the monitoring link. The feeds of monitoring data are defined at least partially based on the monitoring vector definition. Each feed of monitoring data is associated with pharmaceutical order processing. The processor is also configured to receive the plurality of feeds of monitoring data using the monitoring link. The processor is additionally configured to determine a set of monitoring vector data for each of the plurality of feeds of monitoring data. The processor is also configured to identify a monitoring vector signature for each of the plurality of feeds of monitoring data. Each monitoring vector signature defines a range of monitoring vector data is created by a trained predictor. The processor is also configured to identify an anomalous data pattern upon determining that at least one of the set of monitoring vector data is outside the range of the monitoring vector signature for the associated feed of monitoring data. The processor is also configured to transmit an alert indicating that pharmaceutical order processing for the associated feed of monitoring data is anomalous.

In yet another aspect, a method is provided for learning event patterns in pharmaceutical order processing and identifying anomalous events based on learned event patterns. The method is performed by a monitoring server in communication with client computing devices. The monitoring server includes a processor and a memory. The method includes establishing a monitoring link to the plurality of monitored nodes. The monitoring server is configured to define a plurality of feeds of monitoring data from the monitored nodes using the monitoring link. The feeds of monitoring data are defined at least partially based on the monitoring vector definition. Each feed of monitoring data is associated with pharmaceutical order processing. The method also includes receiving the plurality of feeds of monitoring data using the monitoring link. The method additionally includes determining a set of monitoring vector data for each of the plurality of feeds of monitoring data. The method further includes identifying a monitoring vector signature for each of the plurality of feeds of monitoring data, wherein each monitoring vector signature defines a range of monitoring vector data created by a trained predictor. The method also includes identifying an anomalous data pattern upon determining that at least one of the set of monitoring vector data is outside the range of the monitoring vector signature for the associated feed of monitoring data. The method additionally includes transmitting an alert indicating that pharmaceutical order processing for the associated feed of monitoring data is anomalous.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
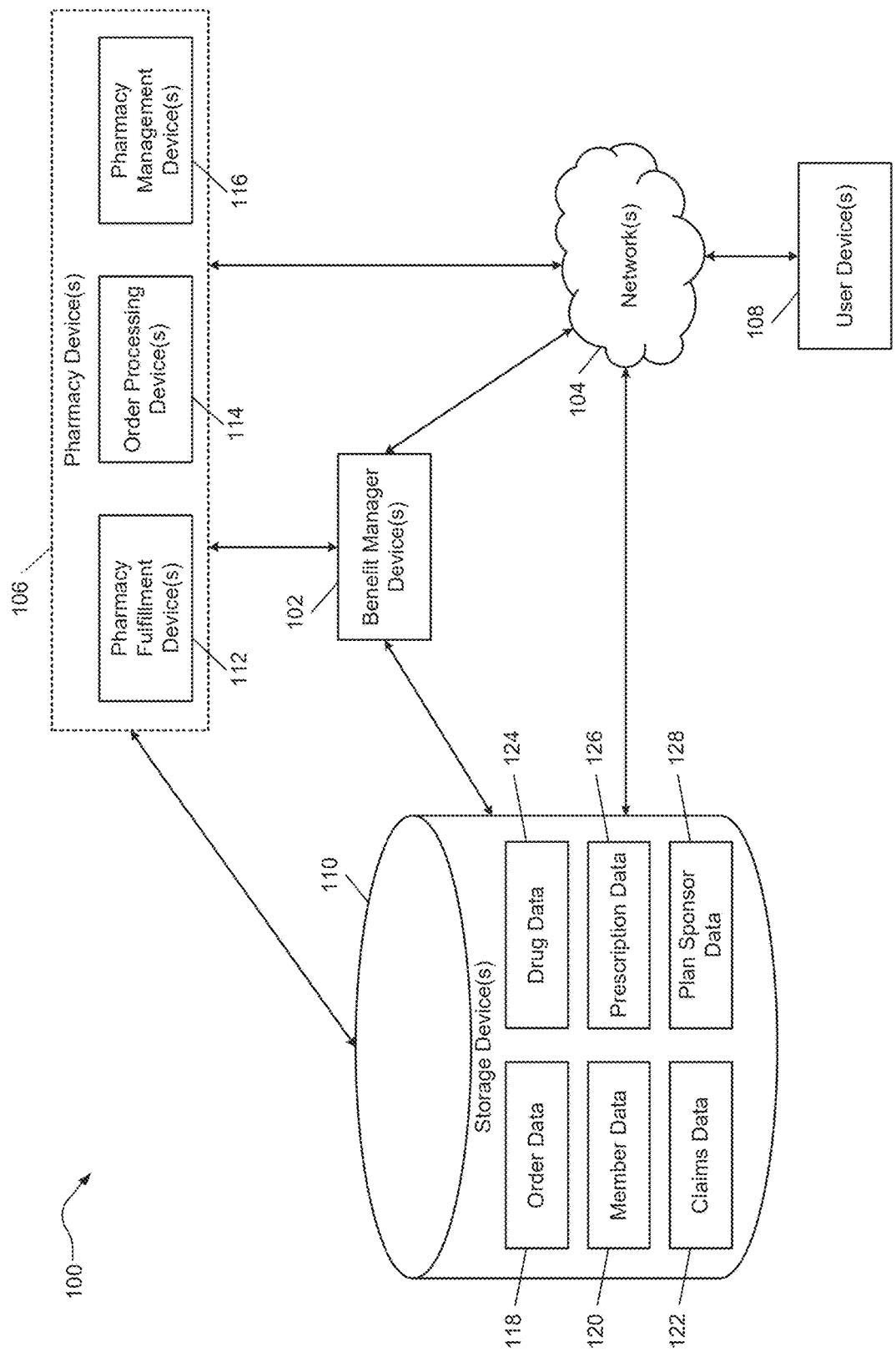
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below. As used herein, "vector data" refers to information that may be captured and analyzed for a particular dimension, node, and/or channel. Vector data may encompass data with, for example: (i) a magnitude (or value) and direction (or trend), (ii) a change in expected magnitude or direction relative to predicted data, and (iii) data relating to a pharmacy, drugs, or other consumables exceeding an expected or defined boundary in magnitude or direction. Thus, in some examples, vector data may include, for example, prescription information, prescription volume, order volume, order amounts, order information, approval volume, approval rates, transaction volume, transaction rates, rejection volume, and rejection rates. For example, prescription volume can increase over time; thus, having a positive direction. Prescription volume can decrease over time; thus, having a negative direction. In another example, a vector may be described based on the breadth and depth of a change in value for a particular unit of data. For example, a vector may include magnitudes and directions of data in examples including: (a) magnitude and direction of prescription amounts of a particular pharmaceutical by a particular physician; (b) magnitude and direction of prescription amounts for a particular pharmaceutical across all prescribers; (c) magnitude and direction of prescription amounts across all prescribers for all pharmaceuticals; (d) magnitude and direction of prescription volumes for a particular drug in a particular pharmacy; (e) magnitude and direction of prescription volumes for a particular drug in all pharmacies; and (f) magnitude and direction of prescription volumes in all pharmacies. In some examples, vectors can be defined based on capturing values of data (e.g., prescription volumes, transaction volumes, rejection rates, rejection volumes, approval rates, approval volumes, new prescriber volumes) across any suitable dimension including, for example: (a) client identifier; (b) carrier identifier; (c) contract identifier; (d) group identifier; (e) prescription pharmaceutical identifier; (f) pharmacy identifier; (g) claim rejection code; (h) member or individual identifier; (i) prescriber or physician identifier; and (j) any combination of the above. As such, the vectors may reflect, for example, the magnitude and trends of prescriptions volumes dispensed at a particular pharmacy for a particular drug (i.e., prescription pharmaceutical identifier and pharmacy identifier) or the overall magnitude and trends of prescriptions at a particular pharmaceutical chain for a particular drug (i.e., prescription pharmaceutical identifier and a particular set of pharmacy identifiers). This approach allows for monitoring of the volume and trends in rejections for all of a particular set of pharmacies (e.g., a region of a chain of pharmacies), volume and trends of fulfilled prescriptions for a particular fulfillment channel (e.g., home delivery), volume and trends in prescribing a newly prescribed drug, or volume and trends for particular rejection types for a particular client.

In complex data systems, new computing devices may be added or changed frequently and dynamically. Further, new classes of data processing may be introduced dynamically or "on-the-fly". While this presents great flexibility, it may also create risks and complications to manage and administer such systems. In the context of pharmacy benefit management ("PBM"), central computing devices are required to orchestrate the processing of pharmaceutical benefits including determining eligibility and providing fulfillment. Such central computing devices may interact with thousands of computing devices representing various parties (e.g., pharmacies, health care providers, and patients) while processing millions of transactions per day. The central computing devices have significant technical difficulties to address when processing such transactions. The transaction volume and customer expectations necessitates that the system must process transactions in seconds or less than a second. However, the system is required to frequently check for problems in pharmaceutical benefit orders that may require rejections. As such, the system is required to apply rule sets to each transaction to determine whether and how to process them. Making matters more complex, the constant addition of new computing devices (e.g., for a new client) or changes to data patterns (e.g., caused by introduction of new prescription pharmaceuticals) requires that these rule sets dynamically and rapidly change. Without such adaptation, the PBM systems are exposed to technical risks of inability to process data at performant speeds and bottle-necking. Nevertheless, in some examples, the rule sets may be improperly defined and cause rejections when they should not. Because of the speed and complexity of processing, it is difficult to determine when conditions have changed in a system that require intervention.

Because of such speed and complexity, there is a significant technical difficulty in determining what constitutes "normal" behavior for a particular set or subset of computing devices. Therefore, obtaining diagnostics or a "pulse" for particular monitoring vector data is essential but technically challenging. (As described herein, the changing conditions and associated data of client computing devices may be referred to as the "pulse" of those devices. In one aspect, the systems and methods may be described as providing a "pulse" for monitored vectors.) For example, newly added pharmaceutical fulfillment programs, pharmacy chains, pharmacy locations, and pharmaceutical drugs may be associated with unique "pulses". Further, past "pulses" may vary significantly over time as societal or economic events change the predicted patterns of data. However, diagnoses of the distinction between "normal" behavior and "anomalous" behavior indicating systemic or technical problems is essential.

The systems and methods described herein address these technical problems by providing a monitoring system that applies machine learning and artificial intelligence to respond to dynamic changes in environments. Such systems identify complex patterns in node vectors and dynamically identifying anomalous or abnormal events that may indicate process failure and/or require technical intervention. Further, these systems and methods allow central systems to monitor client computing devices. In the context of PBMs, the systems and methods provide tracking and monitoring of client computing devices based, for example, on client, carrier, contract, group, pharmaceutical, pharmacy, rejection code, individual/member, prescriber, and other dimensions or attributes. Accordingly, such systems and methods provide tracking and monitoring of the changing status and associated data of client computing devices. As a result, the systems and methods described allow for identification and remediation of anomalous patterns before they become emergent. These solutions may be implemented dynamically with a "plug-and-play" model and/or using user configuration(s). In the context of PBMs, the systems and methods support tracking "pulses" for pharmacy claim processing, eligibility determinations, order fulfillment, digital therapies, and related transactions.

Using the described approach, these systems and methods may, for example, track for rejections of pharmacy claims at thousands of locations from a particular new client and determine whether those rejections are appropriate. The systems and methods also provide the benefit of tracking for trends and developments in PBM data that may allow volume tracking for particular fulfillment models, volume tracking of new pharmaceuticals, or client-specific rejections.

In one example, the systems and methods are implemented with visualization tools including a dashboard to display information for each tracked dimension, rejection or approval trends, volume trends, error trends, changes to client computing devices, and reported (or alerted) anomalies or errors that require intervention. The systems and methods may also be deployed using a configuration portal that may allow for configuration of new clients, alteration of definitions for normal "pulses", and changes to rule sets for approving particular transactions.

The systems and methods provide several technological improvements that are not known in existing technologies. First, the systems and methods provide the ability to monitor multiple feeds of data for multiple channels of monitored nodes simultaneously, and to identify anomalies in respective feeds. Further, the systems and methods provide the ability to create specific monitoring data definitions for each monitored node (or channel of multiple nodes) to define vectors of data (or monitoring vectors of data) for distinct node(s). The systems and methods also provide the ability to apply trained predictors to define monitoring vector signatures for each of the node(s) or channel of nodes. The monitoring vector signatures may, in one example, be trained with the trained predictor learning based on historic monitoring vector data (i.e., previously obtained data from historic feeds associated with previously processed pharmaceutical orders) specific to each node or channel of nodes. The monitoring vector signatures may also be trained using historic result data (i.e., previously obtained data specifying the results of the previously processed pharmaceutical orders specified in the historic monitoring vector data). The monitoring vector signature therefore may provide ranges of monitoring vector data which may be represented as thresholds, boundaries, and definitions for monitoring vector data for particular node(s) or channel(s) during normal processing conditions or normal function. As used herein, the terms "normal processing conditions" or "normal function" or similar terms describe cases or states in which transaction processing is occurring as expected. As used herein, the terms "anomalous processing conditions" or "abnormal processing conditions" or similar terms describe those conditions in which a transaction processing is not occurring as expected. By monitoring deviations from the monitoring vector signature, the systems and methods may provide adaptive methods of ensuring healthy processing and functioning.

In one aspect, a monitoring system is provided for learning event patterns in pharmaceutical order processing and identifying anomalous events based on learned event patterns. The monitoring system may be used for use cases including: (i) tracking and monitoring the approval and rejection of pharmacy claims and the total volume activity for particular clients; (ii) tracking and monitoring deviations from the monitoring vector signature for such data; (iii) alerting users based on such deviations to identify emergent issues in the "pulse" of the monitored node(s) or channel(s); and (iv) adapting the associated monitoring vector signature as needed based on deviations.

The monitoring system may also be used for the use case of: (i) tracking and monitoring the claims activity tied to a particular pharmaceutical including, for example, the number of prescriptions, the number of orders, the number of approvals; (ii) tracking and monitoring deviations from the monitoring vector signature for such data; (iii) alerting users based on such deviations to identify emergent issues in the "pulse" of the monitored node(s) or channel(s); and (iv) adapting the associated monitoring vector signature as needed based on deviations.

The monitoring system may additionally be used for the use case of: (i) tracking and monitoring the claims activity tied to a particular pharmacy or group of pharmacy including, for example, the number of prescriptions, the number of orders, the number of approvals; (ii) tracking and monitoring deviations from the monitoring vector signature for such data; (iii) alerting users based on such deviations to identify emergent issues in the "pulse" of the monitored node(s) or channel(s); and (iv) adapting the associated monitoring vector signature as needed based on deviations.

The monitoring system may also be used for the use case of: (i) tracking and monitoring the claims activity tied to a particular member or group of members including, for example, the number of prescriptions, the number of orders, the number of approvals; (ii) tracking and monitoring deviations from the monitoring vector signature for such data; (iii) alerting users based on such deviations to identify emergent issues in the "pulse" of the monitored node(s) or channel(s); and (iv) adapting the associated monitoring vector signature as needed based on deviations.

In some examples, a node may be defined as a computing device with a particular architecture. To provide the benefits described herein, such nodes may have an architecture including parallel processing cores to address the significant throughput requirements for system. In some examples, nodes may alternatively use serial processors. The nodes may also utilize memory structures to hold transient data including vectors in process. Such memory may include non-volatile persistent storage which provides temporary (short-term) storage until data is moved to a long-term storage device such as a permanent, central database. The short-term storage may utilize I/O buffers. The nodes may also be configurable and may be either physical nodes or virtual nodes that are generated based on corresponding physical nodes using suitable virtualization technologies including hypervisors. In most embodiments, the nodes also have access to suitable networking infrastructure to provide necessary throughput and access to storage.

Based on the above use cases and the descriptions herein, the systems and methods may also provide the ability to monitor and track rejections at varying granular levels, adaptively learn what represents "normal" and retrain models, and provide alerts to users to identify potential systemic or sub-systemic issues that may be causing deviations from the expected monitoring vector signature(s). For example, the systems and methods allow for the monitoring of rejections of a region of pharmacy locations for a large pharmacy, and identify changes in processing state for those locations. The systems and methods also allow comparison between varying similar clients. For example, a newly onboarding pharmacy location may be compared to data for longstanding pharmacy locations to identify relative differences in vector data. Such differences may be used to identify, for example, issues and underlying problems in processing for the newly onboarding pharmacy or the longstanding pharmacy locations. Likewise, the systems and methods described allow for monitoring and testing of the success of new methods of delivering or fulfilling prescriptions by tracking the monitoring vector data for prescriptions from a new program and, for example, comparing that to monitoring vector data for prescriptions for existing programs. Similarly, the systems and methods described allow for monitoring and testing of the success of a new drug or prescription program by comparing associated monitoring vector data for monitoring vector data for similar prescriptions. Likewise, the systems and methods described allow for monitoring and tracking of claim rejection types for particular clients. As described, such vectoring monitoring data is repeatedly used by a machine learning system that applies artificial intelligence to learn from monitoring vector data and define expected data.

The systems and methods may also be configured to use a "touchless" approach that requires little or no human intervention. For example, the monitoring server is configured to identify new patterns in client computing devices and vector data and thereby to discover vector data indicating that: (a) a new client has been added; (b) a new member has been added; (c) a new formulary or pharmaceutical has been added; and (d) a new pharmacy has been added. For example, in on embodiment the feeds of data are routinely processed to identify indications of such new monitoring vector data and, therefore, a newly available feed of data for each new client, new member, new formulary, or new pharmacy. In some examples, the feed of data may provide definitions for the new monitoring vector data upon identifying new data based, for example, on included configuration or metadata files. In other examples, the monitoring server may request or otherwise obtain definitions for new feeds after determining that new monitoring vector data exists. In some examples, a user may provide input to identify such new monitoring vector data and to define, for example, a new client, new member, new formulary, or new pharmacy. In further examples, the monitoring server may also dynamically determine a monitoring vector signature associated with each new feed. In some examples, the monitoring vector signature may be determined dynamically based on similar data feeds. For example, an initial monitoring vector signature for a new client may be created based on a monitoring vector signature for a similar client or an average client and an initial monitoring vector for a new member may be created based on a monitoring vector signature for a similar member or an average member. Likewise, an initial monitoring vector signature for a new formulary may be created based on a monitoring vector signature for a similar formulary or an average formulary. Further, an initial monitoring vector for a new pharmacy may be created based on a monitoring vector signature for a similar pharmacy or an average pharmacy.

In one additional aspect, the systems and methods are self-healing and adaptive because they provide constantly evolving methods of tracking and monitoring data feeds and identifying deviations therefrom. Although in some embodiments, the monitoring vector signature may be edited by users, this approach allows the trained predictor to learn normal patterns and to define monitoring vector signatures for feeds without human intervention. Further, the systems and methods are configured to alert or trigger events based on detected deviations from monitoring vector signatures identified in the feeds.

The monitoring system includes a plurality of client computing devices. Each of the client computing devices including a client processor and a client memory. As described herein, each client computing device may be associated with one or more feeds of monitoring data. However, the monitoring system is configured to obtain monitoring data for each feed from at least one client computing device. In some examples, multiple client computing devices capture portions of data used to create feeds of monitoring data. The monitoring system also includes a monitoring server in communication with the f client computing devices. The monitoring server includes a processor and a memory. In some examples, the monitoring server includes multiple sub-servers and may be represented as a physical server(s) or virtual server(s). In at least some examples, the client computing device(s) may be integrated with the monitoring server(s).

The monitoring server is configured to identify a plurality of monitored nodes from the client computing devices based on a monitoring vector definition. As described herein, the monitoring vector definition may define at least (a) monitoring data to capture for each monitoring data vector; and (b) the physical and/or virtual location to obtain such monitoring data (i.e., from which client computing device(s).

The monitoring server is also configured to establish a monitoring link to the plurality of monitored nodes. The monitoring server is configured to define at least one feed (or a plurality of feeds) of monitoring data from the monitored nodes using the monitoring link. More specifically, the monitoring server may request, receive, or otherwise obtain monitoring data from at least one of the plurality of nodes that includes monitoring data specified in the monitoring vector definition. Thus, the monitoring data in each feed may be obtained from one or more monitored nodes of the plurality of client computing devices. The feeds of monitoring data are defined at least partially based on the monitoring vector definition. In some examples, the feeds may also be defined by a user via a configuration tool or via metadata contained in the feed itself. In an example embodiment, each feed of monitoring data is associated with pharmaceutical order processing. In other examples, the feeds of monitoring data may be associated with related processing for digital therapeutics, billing, or other data processing systems without limitation.

The processor is also configured to receive the plurality of feeds of monitoring data using the monitoring link and to determine a set of monitoring vector data for each of the plurality of feeds of monitoring data. The determined set of monitoring vector data represents obtaining a responsive set of data from the feeds based on the monitoring vector definition. In one example, the monitoring vector definition may designate that a particular feed is to be obtained from a source client computing device A (or node A) and that a first category of data be obtained from client computing device A (or node A). The determined set of monitoring vector data is obtained by processing the first category of data with the monitoring vector definition to obtain necessary fields. (In some examples, the first category of data is obtained in a manner that requires no further processing.) For example, the processor may query or search from each plurality of feed to obtain data including, for example, (i) claims activity tied to a particular pharmaceutical including, for example, the number of prescriptions, the number of orders, the number of approvals; (ii) claims activity tied to a particular pharmacy or group of pharmacy including, for example, the number of prescriptions, the number of orders, the number of approvals; and (iii) claims activity tied to a particular member or group of members including, for example, the number of prescriptions, the number of orders, the number of approvals. In some examples, multiple feeds of data (from one or more client computing devices) may be processed together to obtain the set of monitoring vector data for each of the plurality of feeds of monitoring data.

The processor is also configured to identify a monitoring vector signature for each of the plurality of feeds of monitoring data. In an example embodiment, each monitoring vector signature defines a range of monitoring vector data created by a trained predictor. As described above and herein, the monitoring vector signatures may define expected data associated with prescription processing in non-anomalous or "normal" conditions. In one example, the trained predictor trains each monitoring vector signature as follows: The processor receives or otherwise obtains a plurality of historic monitoring vector data for a first feed of monitoring data. Each of the plurality of historic monitoring vector data is associated with a respective pharmaceutical order. The processor also receives associated historic result data and/or historic condition data indicating whether each element of the first monitored feed was associated with a normal or anomalous state. The processor applies the plurality of historic monitoring vector data and the historic result and/or historic condition data to the trained predictor to identify a first monitoring vector signature for the first feed of monitoring data. The first monitoring vector signature defines a corresponding range of normal monitoring vector data based on a subset of the plurality of historic monitoring vector data associated with respective pharmaceutical orders. Thus the processor applies the trained predictor to "learn" (and later adaptively learn) data patterns for monitoring vector data that indicate normal or anomalous states. In at least one example, the trained predictor applies a deep learning neural network. In other examples, the trained predictor may receive tuning input from a user to parametrically tune the monitoring vector signatures. In additional examples, users may actively define monitoring vector signatures using the user interface and configuration modules described above.

The processor is also configured to identify an anomalous data pattern upon determining that at least one of the set of monitoring vector data is outside the range of the monitoring vector signature for the associated feed of monitoring data. In other words, the processor applies the results of the trained predictor to identify patterns in the "pulse" of each feed and each associated monitoring vector data and identify that a particular channel or node is behaving in an anomalous manner. The processor is additionally configured to transmit an alert indicating that pharmaceutical order processing for the associated feed of monitoring data is anomalous. The alert may be transmitted to any suitable recipient including a user, a configuration screen, a visualizing dashboard, and a remediation computing device configured to diagnose and address underlying issues in the client computing devices.

The processor is also configured to adaptively train each monitoring vector signature based on changing conditions. For example, the processor is configured to process the anomalous data pattern to determine that the monitoring vector signature for the associated feed of monitoring data requires correction. In one example, the processor performs this step by testing a monitoring vector signature. The processor may receive associated state information indicating that the anomalous data pattern was associated with normal conditions and verify that the monitoring vector signature did not include a possibility for such a data pattern being non-anomalous. (Likewise, the processor may train on a "normal" data pattern that coincides with anomalous conditions and verify that the monitoring vector signature did not include a possibility for such a "normal" data pattern being anomalous.) The processor is also configured to apply the anomalous data pattern and the set of result data to the trained predictor to update the monitoring vector signature for the associated feed of monitoring data. In effect, the processor is configured to retrain the monitoring vector signature based on new and non-conformant information.

The processor is also configured to dynamically respond to new feeds of monitoring data. In one example, the processor is configured to determine that the plurality of feeds of monitoring data includes at least one new feed of monitoring data. The processor is also configured to identify a monitoring vector definition for the at least one new feed of monitoring data. As described above, such a monitoring vector definition may be obtained (i) dynamically from the client computing device providing the at least one new feed; (ii) through dynamic discovery of the at least one new feed that may, for example, describe data used to create a monitoring vector definition; and (iii) by direct input from a user or an associated computing device. The processor is also configured to update the monitoring link to include the monitoring vector definition for the at least one new feed of monitoring data and to receive the plurality of feeds of monitoring data using the updated monitoring link. In this manner, the monitoring server may dynamically incorporate new feeds of monitoring data.

Relatedly, the monitoring server is also configured to obtain and use a new monitoring vector signature for newly discovered feeds. For example, the processor is configured to obtain a set of monitoring vector data for the at least one new feed of monitoring data based on the feed of monitoring data as described above. In such examples, the processor is also configured to apply the set of monitoring vector data for the at least one new feed of monitoring data to the trained predictor to determine a new monitoring vector signature for the at least one new feed of monitoring data. Thus, the monitoring server may "learn" a pattern for normal and anomalous behavior for each new feed associated with, for example, a new drug, a new pharmacy, a new fulfillment model, a new client, or a new member.

The monitoring server processor is also configured to identify the monitoring vector definition for the at least one new feed of monitoring data based on dynamic discovery from at least one new client computing device. In some examples, the monitoring server processor is also configured to receive a new signature input describing a range of normal monitoring vector data for the at least one new feed of monitoring data. The monitoring server may also initialize the monitoring vector signature for the at least one new feed of monitoring data based on the new signature input. In this manner, the monitoring server may also define a temporary monitoring vector signature until the monitoring server "learns" a new monitoring vector signature for the new feed.

In some examples, the monitoring data may be "noisy" and include information within that is not meaningful. Noisy data may include data that cannot be processed or interpreted and/or corrupt data. (In this context, "noise" data is the opposite of "signal" data which reflects information that can be processed and from which patterns may be derived.) For particular monitoring data, the expected level of "noise" may vary. Noise may occur when data is highly fluid and/or when new sources of data are introduced. Accordingly, in monitoring data where data noise is known to exist, the systems and methods may include a threshold setting of a maximum level of data noise. In such examples, the monitoring server may disregard the monitored data or transmit an alert when the threshold is exceeded. In such examples, sufficient noise levels may indicate that vectors may need to be redefined. Such alerts or changes may be useful to avoid the risk of detection of false positives. In some examples, the relevant threshold may be established by data mining to analyze past data patterns regarding noise or based on human feedback.

In one example, the monitoring server may process monitoring data differently based on the volume of data. Because vector data necessarily depends upon sufficient volume to observe trends, where there is a low level of data or an erratic volume of data, the monitoring server may define rolling windows or intervals to access data in a raw data form as opposed to a vector data form. For certain niche contexts, this approach may be beneficial to allow the systems and methods to provide analysis where vector data may be difficult to create or process in an efficient manner. Such raw data may include any suitable data described herein and the monitoring server may accordingly track based on suitable information including, for example, prescription drug identifiers, pharmacies, doctors, delivery methods, delivery regions, delivery addresses, members, providers, and insurers.

Generally, the systems and methods described herein are configured to perform at least the following steps: establish a monitoring link to the plurality of monitored nodes, wherein the monitoring server is configured to define a plurality of feeds of monitoring data from the monitored nodes using the monitoring link, the feeds of monitoring data defined at least partially based on the monitoring vector definition, wherein each feed of monitoring data is associated with pharmaceutical order processing; receive the plurality of feeds of monitoring data using the monitoring link; determine a set of monitoring vector data for each of the plurality of feeds of monitoring data; identify a monitoring vector signature for each of the plurality of feeds of monitoring data, wherein each monitoring vector signature defines a range of monitoring vector data created by a trained predictor; identify an anomalous data pattern upon determining that at least one of the set of monitoring vector data is outside the range of the monitoring vector signature for the associated feed of monitoring data; transmit an alert indicating that pharmaceutical order processing for the associated feed of monitoring data is anomalous; process the anomalous data pattern to determine that the monitoring vector signature for the associated feed of monitoring data requires correction; apply the anomalous data pattern and the set of result data to the trained predictor to update the monitoring vector signature for the associated feed of monitoring data; determine that the plurality of feeds of monitoring data includes at least one new feed of monitoring data; identify a monitoring vector definition for the at least one new feed of monitoring data; update the monitoring link to include the monitoring vector definition for the at least one new feed of monitoring data; receive the plurality of feeds of monitoring data using the updated monitoring link; obtain a set of monitoring vector data for the at least one new feed of monitoring data, based on the feed of monitoring data; apply the set of monitoring vector data for the at least one new feed of monitoring data to the trained predictor to determine a new monitoring vector signature for the at least one new feed of monitoring data; identify the monitoring vector definition for the at least one new feed of monitoring data based on dynamic discovery from at least one new client computing device; receive a new signature input describing a range of normal monitoring vector data for the at least one new feed of monitoring data; initialize the monitoring vector signature for the at least one new feed of monitoring data based on the new signature input; receive a plurality of historic monitoring vector data for a first feed of monitoring data, wherein each of the plurality of historic monitoring vector data is associated with a respective pharmaceutical order; and apply the plurality of historic monitoring vector data to the trained predictor to identify a first monitoring vector signature for the first feed of monitoring data, wherein the first monitoring vector signature defines a corresponding range of normal monitoring vector data based on a subset of the plurality of historic monitoring vector data associated with respective pharmaceutical orders.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However, in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118. The order data can provide a data vector that can be processed according to the methods and systems described herein.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably. The member data can provide a data vector that can be processed according to the methods and systems described herein The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included. The claims data 122 can provide a data vector that can be processed according to the methods and systems described herein In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications. The drug data 124 can provide a data vector that can be processed according to the methods and systems described herein The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126. Each of these types of data 118, 120, 122, 126 can be combined to form composite data that is used as vector data.

The plan sponsor data 128 includes information regarding the plan sponsors of the PBM. Examples of the plan sponsor data 128 include company name, company address, contact name, contact telephone number, contact e-mail address, etc.

Figure 2:
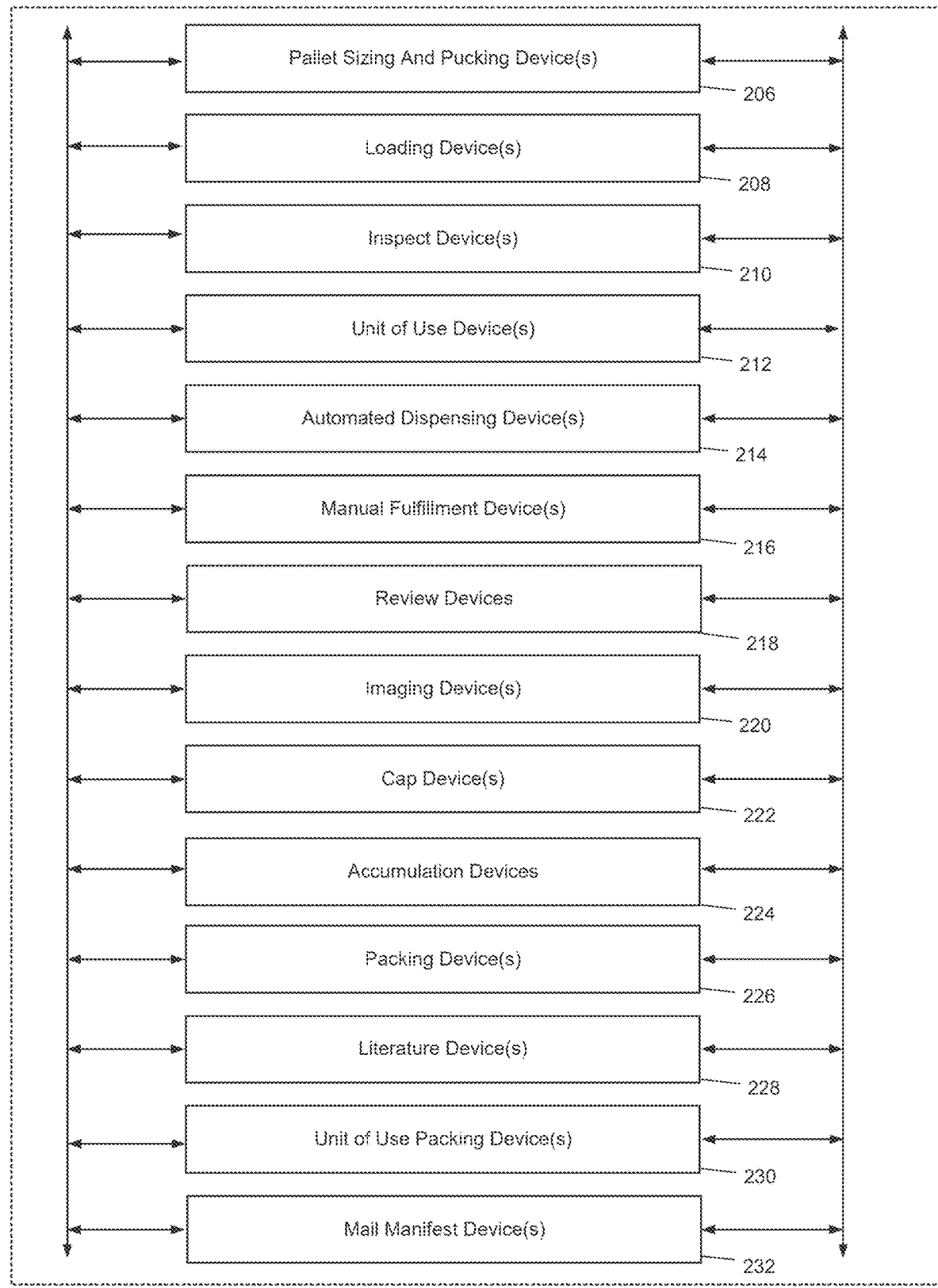
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
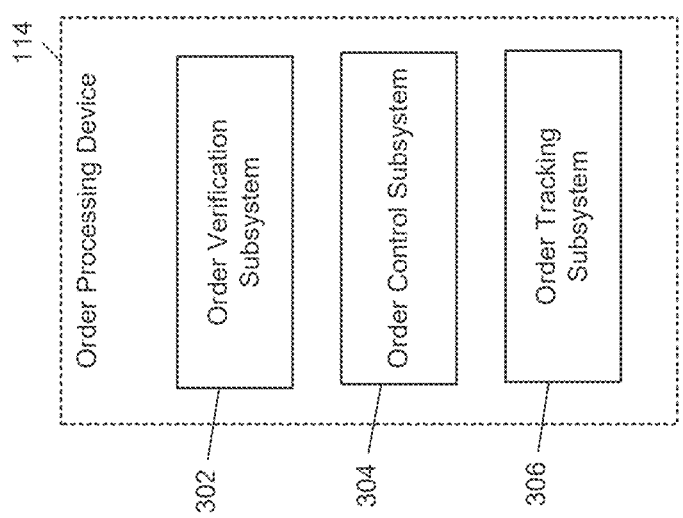
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
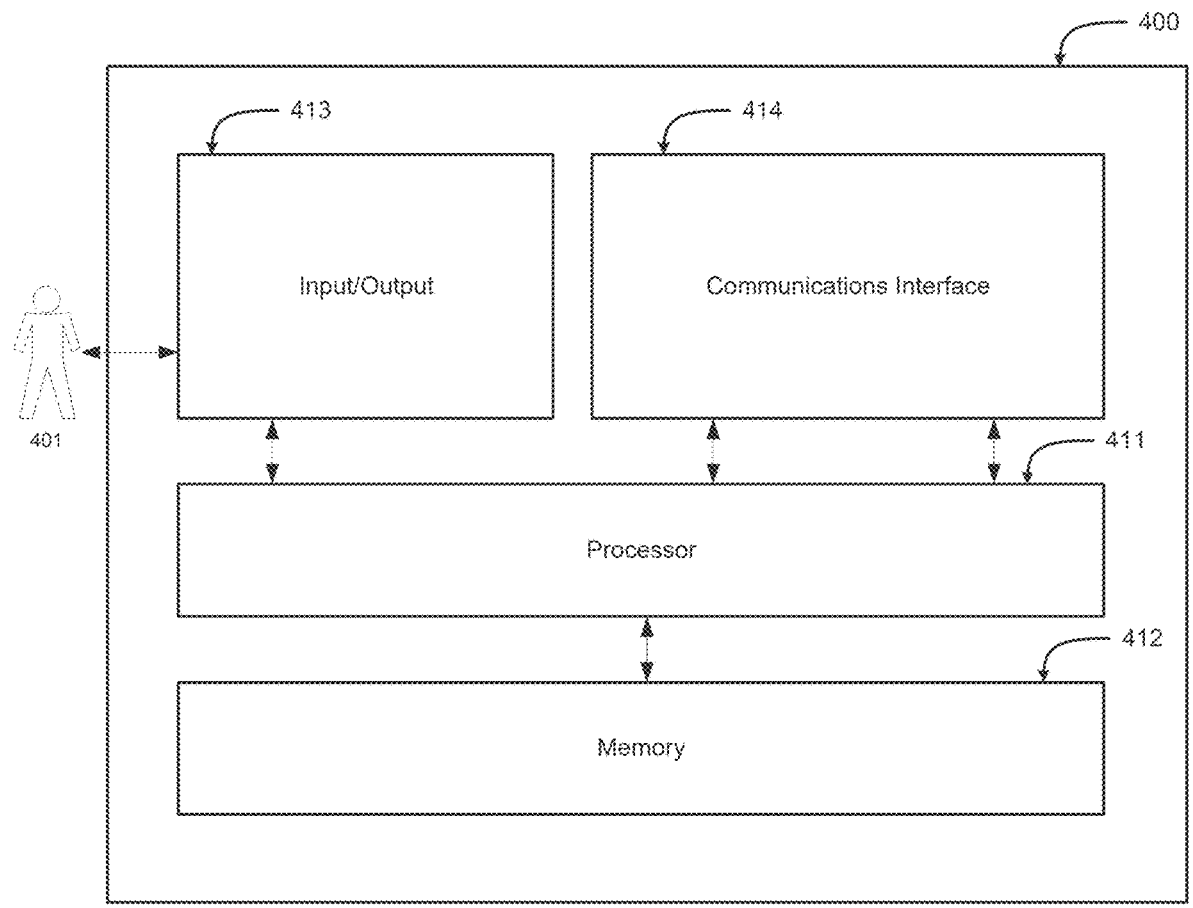
FIG. 4 is a functional block diagram of an example computing device that may be used in the environments described herein.

FIG. 4 is a functional block diagram of an example computing device 400 that may be used in the environments described herein. Specifically, computing device 400 illustrates an exemplary configuration of a computing device. Computing device 400 illustrates an exemplary configuration of a computing device operated by a user 401 in accordance with one embodiment of the present invention.

Computing device 400 may include, but is not limited to, a client computing device and a monitoring server. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of performing the methods for learning event patterns in pharmaceutical order processing and identifying anomalous events based on learned event patterns described herein. In some variations, the characteristics of the described components may be more or less advanced, primitive, or non-functional.

In the exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

Computing device 400 also includes at least one input/output component 413 for receiving information from and providing information to user 401. In some examples, input/output component 413 may be of limited functionality or non-functional as in the case of some wearable computing devices. In other examples, input/output component 413 is any component capable of conveying information to or receiving information from user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

Computing device 400 may also include a communications interface 414, which may be communicatively coupleable to a remote device, such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

Figure 5:
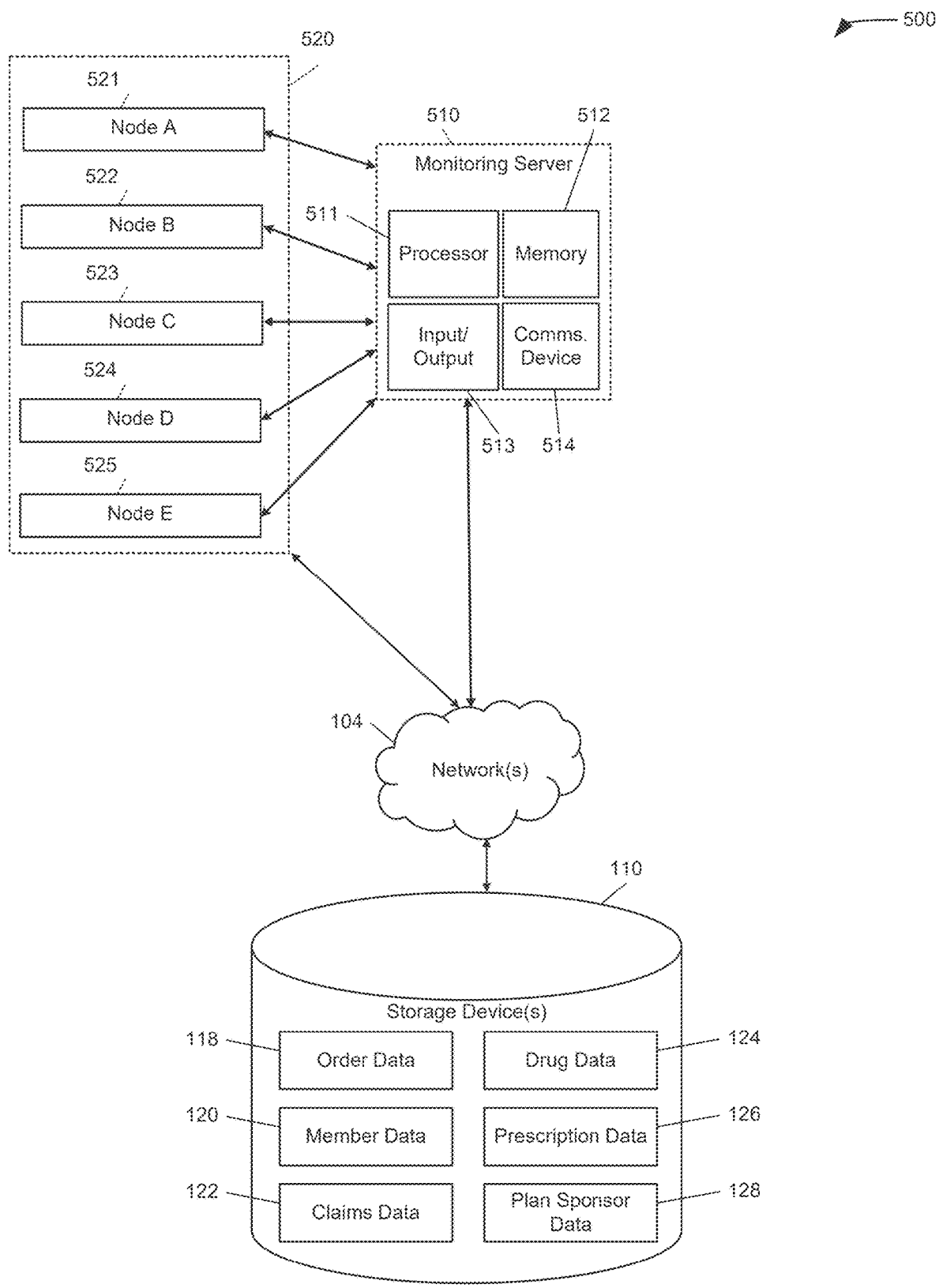
FIG. 5 is a functional block diagram of a monitoring system for learning event patterns in pharmaceutical order processing and identifying anomalous events based on learned event patterns, including multiple computing devices shown in FIG. 4.

FIG. 5 is a functional block diagram of a monitoring system 500 including multiple computing devices similar to computing device 400 (shown in FIG. 4). As described herein, a monitoring system 500 is provided for learning event patterns in pharmaceutical order processing and identifying anomalous events based on learned event patterns. Monitoring system 500 includes a monitoring server 510 further including a processor 511, a memory 512, an input/output 513, and a communications device 514. Monitoring system 500 also includes a plurality of client computing devices 520, distinctly represented as node A 521, node B 522, node C 523, node D 524, and node E 525. Client computing devices 520 are in communication with monitoring server 510. Client computing devices 520 and monitoring server 510 are also in communication with data for the high-volume pharmacy system 100 (shown in FIG. 1) and data stored in storage device 110 via at least network 104. Accordingly, client computing device 520 and monitoring server 510 are able to obtain monitoring data associated with prescription processing for distinct members, clients, pharmacies, pharmaceuticals, and fulfillment models, and to thereby perform the functions described herein.

Figure 6:
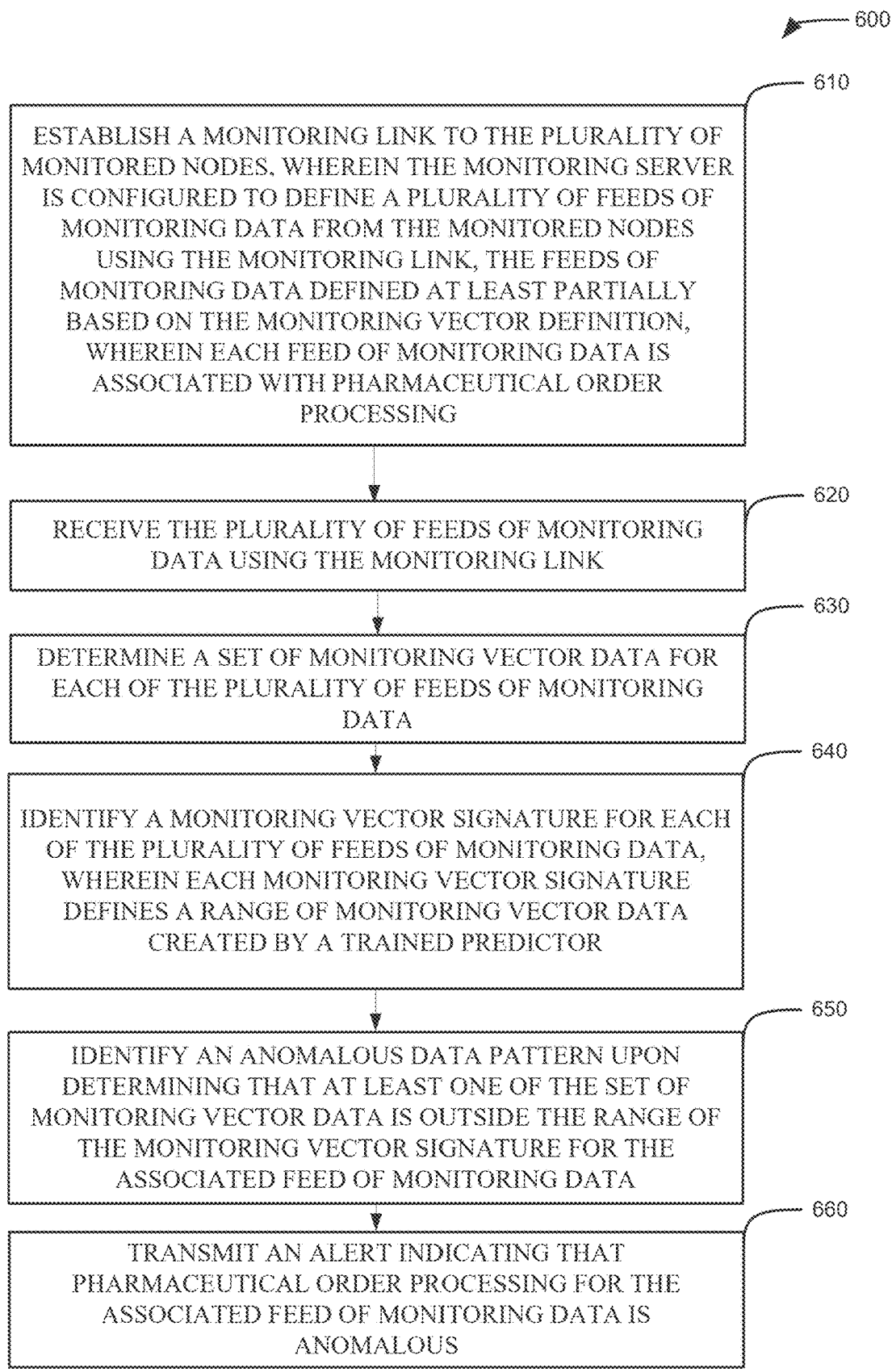
FIG. 6 is a flow diagram representing a method for learning event patterns in pharmaceutical order processing and identifying anomalous events based on learned event patterns performed by the monitoring server of the monitoring system shown in FIG. 5.

FIG. 6 is a flow diagram representing a method 600 for learning event patterns in pharmaceutical order processing and identifying anomalous events based on learned event patterns performed by the monitoring server of the monitoring system 500 (shown in FIG. 5). Specifically, monitoring server 510 is configured to establish 610 a monitoring link to the plurality of monitored nodes 520 (shown in FIG. 5). As described herein, a typical monitored node 520 may be in a one-to-many relationship with vectors such that a particular monitored node 520 may be used to obtain one or more vectors. The number of vectors may vary depending upon, for example, the size and complexity of the vector and the processing capabilities of the node. In some examples, the monitored node may be in a one-to-one relationship with vectors. Similarly, the monitoring server 510 may be in a one-to-many relationship with monitoring nodes 520 or a one-to-one relationship. Monitoring server 510 is configured to define a plurality of feeds of monitoring data from the monitored nodes using the monitoring link. The feeds of monitoring data are defined at least partially based on the monitoring vector definition. In an example embodiment, each feed of monitoring data is associated with pharmaceutical order processing. Monitoring server 510 is also configured to receive 620 the plurality of feeds of monitoring data using the monitoring link. Monitoring server 510 is further configured to determine 630 a set of monitoring vector data for each of the plurality of feeds of monitoring data. Monitoring server 510 is also configured to identify 640 a monitoring vector signature for each of the plurality of feeds of monitoring data. Each monitoring vector signature defines a range of monitoring vector data created by a trained predictor. Monitoring server 510 is also configured to identify 650 an anomalous data pattern upon determining that at least one of the set of monitoring vector data is outside the range of the monitoring vector signature for the associated feed of monitoring data. The range being monitored can represent the quantity of the data or the direction of the data. Monitoring server 510 is also configured to transmit 660 an alert indicating that pharmaceutical order processing for the associated feed of monitoring data is anomalous.

Figure 7:
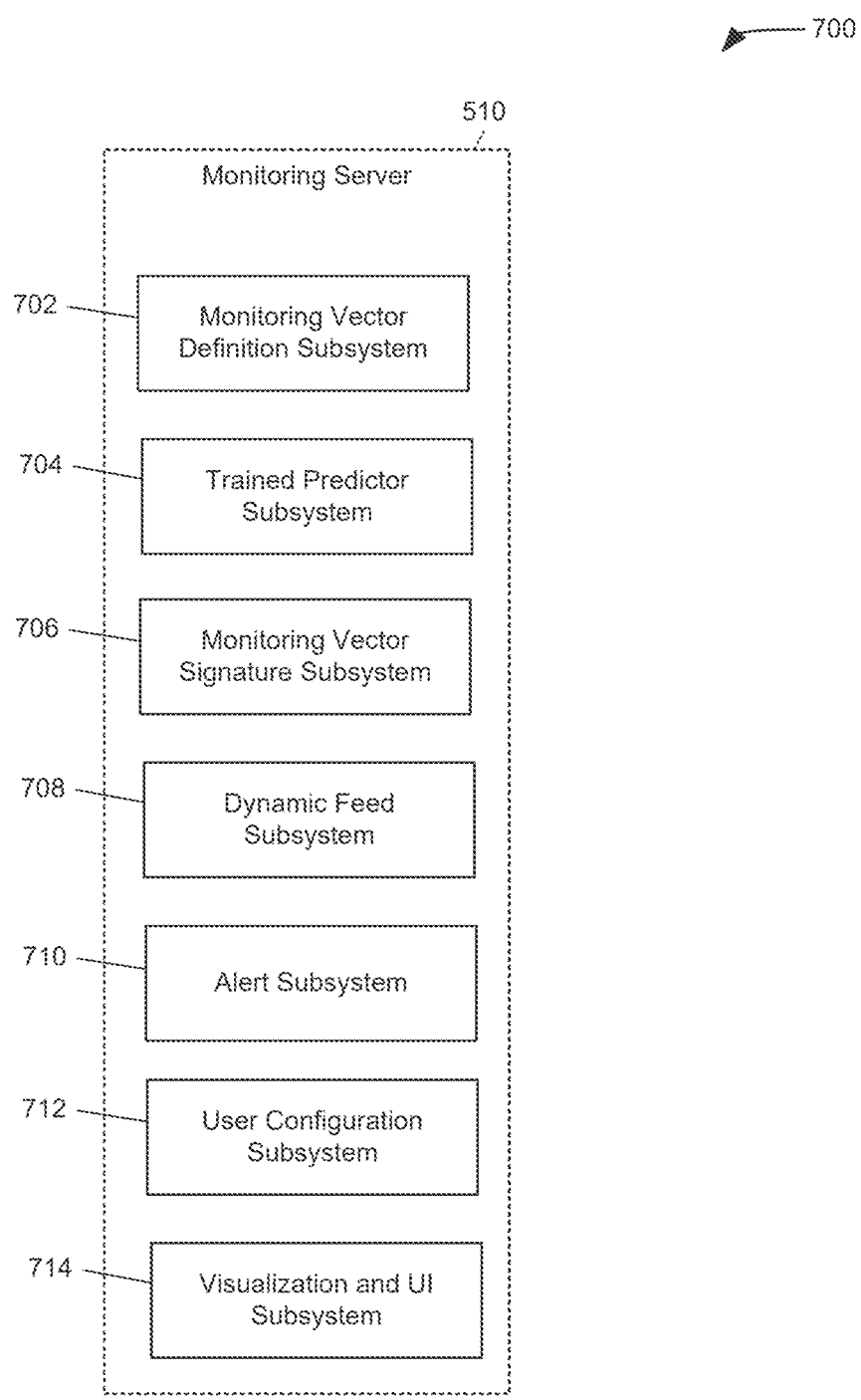
FIG. 7 is a diagram of elements of one or more example computing devices that may be used in the system shown in FIGS. 1-5.

FIG. 7 is a diagram of elements of one or more example computing devices that may be used in the system shown in FIGS. 1-5. As described herein, the elements 702, 704, 706, 708, 710, 712, and 714 are configured to perform the processes and methods described herein. Monitoring vector definition subsystem 702 is configured to provide and allow definition of the monitoring vector definitions used to define the monitoring feeds and monitoring vector data. Trained predictor subsystem 704 is configured to apply the trained predictor to learn and re-learn anomalous patterns for monitoring feeds and to thereby determine the "pulse" of normal and anomalous data patterns. Monitoring vector signature subsystem 706 is configured to define and manage monitoring vector signatures including to create and apply thresholds and boundaries of normal data for each monitoring feed and to determine resultant rules if data is anomalous. For example, anomalous data may be required to recur over a period of time or instances before causing an alert or a retraining. Dynamic feed subsystem 708 is configured to allow dynamic discovery of new clients, members, pharmacies, pharmaceuticals, and other data feeds. Alert subsystem 710 is configured to define rules for alerting users or other systems based on anomalous data. User configuration subsystem 712 is configured to obtain and utilize user configuration information and visualization and user interface ("UI") subsystem 714 is configured to provide visualizations including trend data and alert conditions.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A monitoring system for learning event patterns in pharmaceutical order processing and identifying anomalous events based on learned event patterns, the monitoring system comprising:
a plurality of monitored nodes, the monitored nodes including client processors and client memories; and
a monitoring server in communication with the plurality of monitored nodes, the monitoring server including a processor and a memory, said processor of the monitoring server configured to:
establish a monitoring link to the plurality of monitored nodes, wherein the monitoring server is configured to define a plurality of feeds of monitoring data from the monitored nodes using the monitoring link, the feeds of monitoring data defined at least partially based on a monitoring vector definition, wherein each of the feeds of monitoring data is associated with pharmaceutical order processing;
receive the plurality of feeds of monitoring data using the monitoring link;
determine a set of monitoring vector data for each of the plurality of feeds of monitoring data;
identify that a new feed of the plurality of feeds has been added based on a corresponding set of data of the sets of monitoring vector data being determined to be new, wherein the new feed is associated with a new node of the monitored nodes;
define, by a trained predictor that includes a machine learning model, a monitoring vector signature for each of the plurality of feeds of monitoring data, wherein each monitoring vector signature represents non-anomalous conditions and defines a range of monitoring vector data, wherein to define the monitoring vector signature for the new feed, the trained predictor
identifies a similar monitoring node from the plurality of monitored nodes that is similar to the new node, and
creates the monitoring vector signature for the new feed based on the monitoring vector signature of the similar monitoring node;
identify an anomalous data pattern upon determining that at least one of the sets of monitoring vector data is outside the range of the monitoring vector signature for an associated feed of the plurality of feeds of monitoring data;
transmit an alert indicating that pharmaceutical order processing for the associated feed of monitoring data is anomalous and avoid activation of an automatic fulfillment of a pharmaceutical order associated with the associated feed;
identify a non-anomalous data pattern associated with a non-anomalous feed of the plurality of feeds based on determining that at least one of the sets of monitoring vector data associated with the non-anomalous feed is inside the range of the monitoring vector signature for the non-anomalous feed; and
execute an automated-fill of a pharmaceutical order associated with the non-anomalous feed by controlling a machine.

2. The monitoring system of claim 1, wherein the processor is further configured to:
process the anomalous data pattern to determine that the monitoring vector signature for the associated feed requires correction; and
apply the anomalous data pattern and a set of result data to the trained predictor to update the monitoring vector signature for the associated feed.

3. The monitoring system of claim 1, wherein the processor is further configured to:
receive a plurality of historic monitoring vector data for a first feed of monitoring data, wherein each of the plurality of historic monitoring vector data is associated with a respective pharmaceutical order; and
apply the plurality of historic monitoring vector data to the trained predictor to identify a first monitoring vector signature for the first feed of monitoring data, wherein the first monitoring vector signature defines a corresponding range of normal monitoring vector data based on a subset of the plurality of historic monitoring vector data associated with the respective pharmaceutical order.

4. A monitoring server for learning event patterns in pharmaceutical order processing and identifying anomalous events based on learned event patterns, the monitoring server in communication with a plurality of monitored nodes, the monitoring server including a processor and a memory, said processor configured to:
  establish a monitoring link to the plurality of monitored nodes, wherein the monitoring server is configured to define a plurality of feeds of monitoring data from the monitored nodes using the monitoring link, the feeds of monitoring data defined at least partially based on a monitoring vector definition, wherein each of the feeds of monitoring data is associated with pharmaceutical order processing;
  receive the plurality of feeds of monitoring data using the monitoring link;
  determine a set of monitoring vector data for each of the plurality of feeds of monitoring data;
  identify that a new feed of the plurality of feeds has been added based on a corresponding set of data of the sets of monitoring vector data being determined to be new, wherein the new feed is associated with a new node of the monitored nodes;
  define, by a trained predictor that includes a machine learning model, a monitoring vector signature for each of the plurality of feeds of monitoring data, wherein each monitoring vector signature represents non-anomalous conditions and defines a range of monitoring vector data, wherein to define the monitoring vector signature for the new feed, the trained predictor
    identifies a similar monitoring node from the plurality of monitored nodes that is similar to the new node, and
    creates the monitoring vector signature for the new feed based on the monitoring vector signature of the similar monitoring node;
  identify an anomalous data pattern upon determining that at least one of the sets of monitoring vector data is outside the range of the monitoring vector signature for an associated feed of the plurality of feeds of monitoring data;
  transmit an alert indicating that pharmaceutical order processing for the associated feed of monitoring data is anomalous and avoid activation of an automatic fulfillment of a pharmaceutical order associated with the associated feed;
  identify a non-anomalous data pattern associated with a non-anomalous feed of the plurality of feeds based on determining that at least one of the sets of monitoring vector data associated with the non-anomalous feed is inside the range of the monitoring vector signature for the non-anomalous feed; and
  execute an automated-fill of a pharmaceutical order associated with the non-anomalous feed by controlling a machine.

5. The monitoring server of claim 4, wherein the processor is further configured to:
  process the anomalous data pattern to determine that the monitoring vector signature for the associated feed requires correction; and
  apply the anomalous data pattern and a set of result data to the trained predictor to update the monitoring vector signature for the associated feed.

6. The monitoring server of claim 4, wherein the processor is further configured to:
  receive a plurality of historic monitoring vector data for a first feed of monitoring data, wherein each of the plurality of historic monitoring vector data is associated with a respective pharmaceutical order; and
  apply the plurality of historic monitoring vector data to the trained predictor to identify a first monitoring vector signature for the first feed of monitoring data, wherein the first monitoring vector signature defines a corresponding range of normal monitoring vector data based on a subset of the plurality of historic monitoring vector data associated with the respective pharmaceutical order.

7. The monitoring system of claim 1, wherein a respective set of the monitoring vector data of the sets of monitoring vector data associated with a respective feed of the plurality of feeds includes:
  a magnitude and direction of the respective feed,
  a change in expected magnitude of the respective feed or change of the respective feed relative to predicted data, and
  data relating to a pharmacy associated with the respective feed, drugs associated with the respective feed, or other consumables associated with the respective feed exceeding a defined boundary in magnitude or direction.

8. The monitoring system of claim 7, wherein the respective set of the monitoring vector data includes prescription information, prescription volume, order volume, order amounts, order information, approval volume, approval rates, transaction volume, transaction rates, rejection volume, and rejection rates.

9. The monitoring system of claim 7, wherein a respective monitoring vector signature of the monitoring vector signatures defines ranges of monitoring vector data of the respective feed during normal processing conditions, and
  wherein the processor is further configured to determine if an anomaly exists in the respective feed by comparing the ranges of respective monitoring vector signature to the respective set of the monitoring vector data.

10. The monitoring system of claim 1, wherein the processor is further configured to:
  receive state information from the new node;
  verify that the monitoring vector signature for the new feed failed to indicate an identified state of the state information, wherein the state is one or more of an anomalous condition or a non-anomalous condition; and
  update, with the trained predictor, the monitoring vector signature for the new feed based on the identified state.

11. The monitoring server of claim 4, wherein a respective set of the monitoring vector data of the sets of monitoring vector data associated with a respective feed of the plurality of feeds includes:
  a magnitude and direction of the respective feed,
  a change in expected magnitude of the respective feed or change of the respective feed relative to predicted data, and
  data relating to a pharmacy associated with the respective feed, drugs associated with the respective feed, or other consumables associated with the respective feed exceeding a defined boundary in magnitude or direction.

12. The monitoring server of claim 11, wherein the respective set of the monitoring vector data includes prescription information, prescription volume, order volume, order amounts, order information, approval volume, approval rates, transaction volume, transaction rates, rejection volume, and rejection rates.

13. The monitoring server of claim 11, wherein a respective monitoring vector signature of the monitoring vector signatures defines ranges of monitoring vector data of the respective feed during normal processing conditions, and
wherein the processor is further configured to determine if an anomaly exists in the respective feed by comparing the ranges of respective monitoring vector signature to the respective set of the monitoring vector data.

14. The monitoring server of claim 4, wherein the processor is further configured to:
receive state information from the new node;
verify that the monitoring vector signature for the new feed failed to indicate an identified state of the state information, wherein the state is one or more of an anomalous condition or a non-anomalous condition; and
update, with the trained predictor, the monitoring vector signature for the new feed based on the identified state.

15. A method for learning event patterns in pharmaceutical order processing and identifying anomalous events based on learned event patterns, the method performed by a monitoring server in communication with a plurality of monitored nodes, the monitoring server including a processor and a memory, said method comprising:
establishing a monitoring link to the plurality of monitored nodes, wherein the monitoring server is configured to define a plurality of feeds of monitoring data from the monitored nodes using the monitoring link, the feeds of monitoring data defined at least partially based on a monitoring vector definition, wherein each of the feeds of monitoring data is associated with pharmaceutical order processing;
receiving the plurality of feeds of monitoring data using the monitoring link;
determining a set of monitoring vector data for each of the plurality of feeds of monitoring data;
identifying that a new feed of the plurality of feeds has been added based on a corresponding set of data of the sets of monitoring vector data being determined to be new, wherein the new feed is associated with a new node of the monitored nodes;
defining, by a trained predictor that includes a machine learning model, a monitoring vector signature for each of the plurality of feeds of monitoring data, wherein each monitoring vector signature represents non-anomalous conditions and defines a range of monitoring vector data, wherein the defining the monitoring vector signature for the new feed includes the trained predictor:
identifying a similar monitoring node from the plurality of monitored nodes that is similar to the new node, and
creating the monitoring vector signature for the new feed based on the monitoring vector signature of the similar monitoring node;
identifying an anomalous data pattern upon determining that at least one of the sets of monitoring vector data is outside the range of the monitoring vector signature for an associated feed of the plurality of feeds of monitoring data;
transmitting an alert indicating that pharmaceutical order processing for the associated feed of monitoring data is anomalous and avoid activation of an automatic fulfillment of a pharmaceutical order associated with the associated feed;
identifying a non-anomalous data pattern associated with a non-anomalous feed of the plurality of feeds based on determining that at least one of the sets of monitoring vector data associated with the non-anomalous feed is inside the range of the monitoring vector signature for the non-anomalous feed; and
executing an automated-fill of a pharmaceutical order associated with the non-anomalous feed by controlling a machine.

16. The method of claim 15, further comprising:
processing the anomalous data pattern to determine that the monitoring vector signature for the associated feed requires correction; and
applying the anomalous data pattern and a set of result data to the trained predictor to update the monitoring vector signature for the associated feed.

17. The method of claim 15, further comprising:
receiving a plurality of historic monitoring vector data for a first feed of monitoring data, wherein each of the plurality of historic monitoring vector data is associated with a respective pharmaceutical order; and
applying the plurality of historic monitoring vector data to the trained predictor to identify a first monitoring vector signature for the first feed of monitoring data, wherein the first monitoring vector signature defines a corresponding range of normal monitoring vector data based on a subset of the plurality of historic monitoring vector data associated with the respective pharmaceutical order.

18. The method of claim 15, wherein a respective set of the monitoring vector data of the sets of monitoring vector data associated with a respective feed of the plurality of feeds includes:
a magnitude and direction of the respective feed,
a change in expected magnitude of the respective feed or change of the respective feed relative to predicted data, and
data relating to a pharmacy associated with the respective feed, drugs associated with the respective feed, or other consumables associated with the respective feed exceeding a defined boundary in magnitude or direction.

19. The method of claim 18, wherein the respective set of the monitoring vector data includes prescription information, prescription volume, order volume, order amounts, order information, approval volume, approval rates, transaction volume, transaction rates, rejection volume, and rejection rates.

20. The method of claim 18, wherein a respective monitoring vector signature of the monitoring vector signatures defines ranges of monitoring vector data of the respective feed during normal processing conditions, and
wherein the method further includes determining if an anomaly exists in the respective feed by comparing the ranges of respective monitoring vector signature to the respective set of the monitoring vector data.

* * * * *